US009913795B2

(12) United States Patent
Bernet et al.

(10) Patent No.: US 9,913,795 B2
(45) Date of Patent: *Mar. 13, 2018

(54) COSMETIC COMPOSITIONS CONTAINING SILICONES

(71) Applicant: Dow Corning Corporation, Midland, MI (US)

(72) Inventors: Claire-Sophie Bernet, Brussels (BE); Pinar Cetin, Istanbul (TR); Olivia De Paepe, Dour (BE); Laurence Gallez, Jurbise (BE); Sinem Sevinc, Istanbul (TR)

(73) Assignee: Dow Corning Corporation, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/909,276

(22) PCT Filed: Aug. 6, 2014

(86) PCT No.: PCT/EP2014/066875
§ 371 (c)(1),
(2) Date: Feb. 1, 2016

(87) PCT Pub. No.: WO2015/018853
PCT Pub. Date: Feb. 12, 2015

(65) Prior Publication Data
US 2016/0184214 A1 Jun. 30, 2016

(30) Foreign Application Priority Data

Aug. 9, 2013 (GB) .................................. 1314284.9

(51) Int. Cl.
| | |
|---|---|
| *A61K 8/89* | (2006.01) |
| *A61K 8/25* | (2006.01) |
| *A61Q 5/02* | (2006.01) |
| *A61Q 5/06* | (2006.01) |
| *A61Q 5/10* | (2006.01) |
| *A61Q 5/12* | (2006.01) |
| *A61K 8/891* | (2006.01) |
| *A61K 8/895* | (2006.01) |
| *A61K 8/06* | (2006.01) |
| *A61Q 1/02* | (2006.01) |
| *A61Q 1/14* | (2006.01) |
| *A61Q 9/02* | (2006.01) |
| *A61Q 11/00* | (2006.01) |
| *A61Q 90/00* | (2009.01) |

(52) U.S. Cl.
CPC .............. *A61K 8/89* (2013.01); *A61K 8/062* (2013.01); *A61K 8/25* (2013.01); *A61K 8/891* (2013.01); *A61K 8/895* (2013.01); *A61Q 1/02* (2013.01); *A61Q 1/14* (2013.01); *A61Q 5/02* (2013.01); *A61Q 5/065* (2013.01); *A61Q 5/10* (2013.01); *A61Q 5/12* (2013.01); *A61Q 9/02* (2013.01); *A61Q 11/00* (2013.01); *A61Q 90/00* (2013.01)

(58) Field of Classification Search
None
See application file for complete search history.

(56) References Cited

U.S. PATENT DOCUMENTS

| | | |
|---|---|---|
| 3,424,545 A | 1/1969 | Bauman |
| 3,959,175 A | 5/1976 | Smith, Jr. et al. |
| 4,894,177 A | 1/1990 | Starch |
| 4,978,471 A | 12/1990 | Starch |
| 5,045,225 A | 9/1991 | Aronson et al. |
| 5,229,033 A | 6/1993 | Nguyen et al. |
| 5,562,862 A | 10/1996 | Berzansky, Jr. et al. |
| 5,777,059 A | 7/1998 | Datz-Siegel et al. |
| 6,124,490 A | 9/2000 | Gormley et al. |
| 6,165,968 A | 12/2000 | Lenoble |
| 6,180,712 B1 | 1/2001 | Ishikawa et al. |
| 6,512,015 B1 | 1/2003 | Elms et al. |
| 6,521,586 B1 | 2/2003 | Hoogland et al. |
| 6,521,587 B1 | 2/2003 | L'Hostis et al. |
| 6,656,975 B1 | 12/2003 | Christiano et al. |
| 7,407,991 B2 * | 8/2008 | Creutz ............... B01D 19/0404 510/222 |
| 7,550,514 B2 | 6/2009 | Rautschek et al. |
| 7,619,043 B2 | 11/2009 | Rautschek et al. |
| 7,632,890 B2 | 12/2009 | Creutz et al. |
| 8,084,566 B2 | 12/2011 | Rautschek et al. |
| 8,138,294 B2 | 3/2012 | Henning et al. |
| 8,222,303 B2 | 7/2012 | Herzig et al. |

(Continued)

FOREIGN PATENT DOCUMENTS

| | | |
|---|---|---|
| DE | 102006044839 | 4/2008 |
| EP | 0210731 | 2/1987 |

(Continued)

OTHER PUBLICATIONS

Kosmos, "Hair Color Correcting Tips", Jun. 2012.*
Farn, Richard J. Chemistry and Technology of Surfactants: 2006. Google Books. Accessed Jun. 2015.
Wu, Wen-Zhong. Environmental Behavior and Ecotoxicological Impact of Persistent Organic Pollutants (POP) in Wildlife, with Special Emphasis on the Aquatic Ecosystem. Germany, 1999. Google Books. Web. Apr. 2016.
English language abstract and machine assisted English translation for WO2008145423 extracted from http://www.worldwide.espacenet.com database,13 pages.
International Search Report, PCT/US2012/050977, dated Nov. 16, 2012, 3 pages.

(Continued)

*Primary Examiner* — Brian Gulledge
(74) *Attorney, Agent, or Firm* — Warner Norcross & Judd LLP

(57) ABSTRACT

A cosmetic composition comprising a cosmetically active ingredient in a cosmetically acceptable medium, wherein the cosmetic composition contains a silicone composition comprising (A) a hydrophobic organopolysiloxane fluid having a surface tension of from 15 to 40 mN/m and (B) a finely divided solid hydrophobic filler dispersed in the organopolysiloxane fluid (A).

20 Claims, No Drawings

(56) References Cited

U.S. PATENT DOCUMENTS

| | | |
|---|---|---|
| 8,536,109 B2 | 9/2013 | Delbrassinne et al. |
| 8,633,147 B2 | 1/2014 | Paul et al. |
| 8,653,214 B2 | 2/2014 | Venzmer et al. |
| 8,673,985 B2 | 3/2014 | Lange et al. |
| 8,785,587 B2 | 7/2014 | Wagner et al. |
| 9,175,141 B2 | 11/2015 | Wray et al. |
| 9,487,736 B2 * | 11/2016 | Gallez .................. C11D 3/0026 |
| 2001/0009896 A1 | 7/2001 | Hoogland et al. |
| 2003/0056301 A1 | 3/2003 | Dekker et al. |
| 2007/0161539 A1 | 7/2007 | Hernandez |
| 2008/0021152 A1 | 1/2008 | Rautschek et al. |
| 2008/0021182 A1 | 1/2008 | Jones |
| 2009/0069522 A1 | 3/2009 | Hessefort et al. |
| 2010/0093598 A1 | 4/2010 | Davio et al. |
| 2010/0233104 A1 | 9/2010 | Drake et al. |
| 2011/0056249 A1* | 3/2011 | Cho ..................... D06F 35/006 68/139 |
| 2012/0329701 A1 | 12/2012 | Paul |
| 2013/0309498 A1 | 11/2013 | Chao et al. |
| 2013/0327364 A1 | 12/2013 | Delbrassinne et al. |
| 2015/0038388 A1 | 2/2015 | Gallez et al. |

FOREIGN PATENT DOCUMENTS

| | | |
|---|---|---|
| EP | 0496510 | 7/1992 |
| EP | 0811584 A1 | 12/1997 |
| EP | 1075864 | 2/2001 |
| EP | 1121089 B1 | 8/2001 |
| JP | H04279513 A | 10/1992 |
| JP | 08192001 | 7/1996 |
| JP | 3109122 B2 | 11/2000 |
| JP | 2002053440 | 2/2002 |
| WO | WO9100763 | 1/1991 |
| WO | 1999032539 | 7/1999 |
| WO | 2004047779 | 6/2004 |
| WO | WO2005058454 A1 | 6/2005 |
| WO | WO2005058455 A1 | 6/2005 |
| WO | WO2006063483 | 6/2006 |
| WO | WO2008145423 A1 | 12/2008 |
| WO | WO 2012/134651 * 10/2012 ............... C11D 3/00 |
| WO | WO2012134651 | 10/2012 |
| WO | WO2013122619 A1 | 8/2013 |

OTHER PUBLICATIONS

International Search Report, PCT/US2012/025474, dated Jun. 1, 2012, 4 pages.

Woodward, Roger P., "Surface Tension Measurements Using the Drop Shape Method," First Ten Angstroms, 465 Dinwiddie Street, Portsmouth, VA 23704, pp. 1-6.

Kuo, Dr. Alex C.M., Dow Corning Corporation, "Silicone Release Coatings for the Pressure Sensitive Industry-Overview and Trends; Part I—An Introduction to Silicone", May 2004, pp. 1-4.

Schwartz, et al, "Surface-Active Agents and Detergents," vols. I and II.

"Solid Surface Energy Data (SFE) for Common Polymers", http://www.surface-tension.de/solid-surface-energy.htm, last updated Nov. 20, 2007, printed Mar. 21, 2014, 2 pages.

Surface Energy Data for PDMS: Polydimethylsiloxane, CAS #9016-00-6, Diversified Enterprises, 2009, 1 page.

English language abstract and machine translation for JPH04279513 (A) extracted from http://worldwide.espacenet.com database on Jan. 17, 2018, 5 pages.

English language abstract and machine translation for JP3109122 (B2) extracted from http://worldwide.espacenet.com database on Jan. 17, 2018, 6 pages.

* cited by examiner

COSMETIC COMPOSITIONS CONTAINING SILICONES

This application is a national stage entry of International Patent Application No. PCT/EP2014/66875, filed Aug. 6, 2014, which claims the benefit of GB patent application No. 1314284.9 filed Aug. 9, 2013.

This disclosure relates to cosmetic compositions comprising a cosmetically active ingredient in a cosmetically acceptable medium. Cosmetic compositions include those compositions which are intended to be placed in contact with the external parts of the human body (skin (epidermis), hair system, nails, mucosa, etc., also referred to as "keratinous substrates") or with the teeth and the mucous membranes of the oral cavity with a view exclusively or mainly to cleaning them, perfuming them, changing their appearance, protecting them, keeping them in good condition or correcting body odours. Silicones are widely known in cosmetic compositions. We have found according to the invention that certain silicone compositions have various advantages when used in cosmetic compositions.

A cosmetic composition according to the invention, comprising a cosmetically active ingredient in a cosmetically acceptable medium, contains a silicone composition comprising (A) a hydrophobic organopolysiloxane fluid having a surface tension of from 18 to 40 mN/m and (B) a finely divided solid hydrophobic filler dispersed in the organopolysiloxane fluid (A).

The surface tension of the hydrophobic fluid (A) is measured by the drop shape method, unless otherwise indicated. In this test, a drop of pure hydrophobic fluid is made in air by using a syringe and the surface tension is calculated from measurements of the pendant drop curvature. The drop shape test method is explained in the paper 'Surface tension measurements using the drop shape method' by R. P. Woodward published by First Ten Angstroms of 465 Dinwiddie Street, Portsmouth, Va., U.S.A. In some instances, the surface tension indicated is obtained from the raw material supplier.

A method according to the invention of producing a cosmetic composition comprises (i) preparing a silicone composition by dispersing a finely divided solid hydrophobic filler in a hydrophobic organopolysiloxane fluid having a surface tension of from 18 to 40 mN/m and (ii) mixing the resulting silicone composition with a cosmetically active ingredient in a cosmetically acceptable medium to produce the cosmetic composition.

Examples of cosmetic compositions according to the invention include shampoos, shower gels, conditioning compositions, colouring products, shaving products, personal washing products, mouth washes, face washes, foam colours, foam make up, make up remover, face masks, exfoliating products and tonics. Many of these, for example shampoo, shower gel, shaving product, personal washing product, mouth wash, face wash, foam color, foam make up remover and exfoliating product are foamable compositions which form a foam or lather on the skin or hair, for example upon lathering or rubbing on skin or hair, with or without water, or when dispensed from the container. Such compositions usually contain a detersive surfactant, which is understood to be a surfactant which serves the purpose of cleansing, washing, removing dirt, sebum or make up from the skin or hair substrate. The silicone composition of the invention has particular benefit as a rinsing aid in such foamable compositions. After the cosmetic composition has been applied to the skin or hair and agitated to form a lather, the lather has to be rinsed off. The silicone composition of the invention reduces the amount of water required to rinse off the lather, resulting in a major reduction in water usage; often 60-80% water used by the consumer in shampooing hair is used to rinse hair for removal of lather. The consumer also has a saving in time of rinsing, and less loss of constituents of the cosmetic composition other than surfactants. For example, more effective rinsing with less water after shampooing would allow removal of less perfume, which consumers may perceive as improved cleanliness of their hair.

The silicone composition of the invention has further benefits in cosmetic compositions, which are seen in both foamable compositions and non-foaming compositions such as conditioning compositions, colouring products, make up removers, face masks and tonics. The silicone composition comprising (A) a hydrophobic organopolysiloxane fluid having a surface tension of from 18 to 40 mN/m and (B) a finely divided solid hydrophobic filler dispersed in the organopolysiloxane fluid (A) can for example be used in a shampoo, conditioning composition or colouring product to facilitate combing or improve color retention of hair which has been treated with the shampoo, conditioning composition or colouring product.

The silicone composition comprising (A) a hydrophobic organopolysiloxane fluid having a surface tension of from 18 to 40 mN/m and (B) a finely divided solid hydrophobic filler dispersed in the organopolysiloxane fluid (A) can alternatively be used in a shampoo, conditioning composition or colouring product to increase the smoothness, silkiness and/or shine or improve color retention of hair which has been treated with the shampoo, conditioning composition or colouring product.

The hydrophobic organopolysiloxane fluid (A) having a surface tension of from 18 to 40 mN/m may for example contain aryl or aralkyl groups bonded to Si atoms of the organopolysiloxane and/or alkyl substituents having 4 to 36 carbon atoms bonded to Si atoms of the organopolysiloxane and/or carboxyalkyl groups esterified by an alkyl group having 4 to 36 carbon atoms. The hydrophobic organopolysiloxane fluid can for example be a predominantly linear polydiorganosiloxane but may contain branching; for example 0 to 10% of the siloxane units of the hydrophobic organopolysiloxane fluid may be branching units.

According to one aspect of the invention the hydrophobic organopolysiloxane fluid (A) has a surface tension $\geq 21$ mN/m, for example $\geq 24$ mN/m, alternatively a surface tension $\gamma$ of from 27 to 40 mN/m ($27 \leq \gamma(A) \leq 40$ mN/m). When a silicone composition comprising (A) a hydrophobic organopolysiloxane fluid having a surface tension of from 24 or 27 to 40 mN/m and (B) a finely divided solid hydrophobic filler dispersed in the organopolysiloxane fluid (A) is incorporated in a foamable cosmetic composition, it has no or very little effect on the foamability of the composition but does facilitate rinsing, removing the lather using less water and in a shorter time. This is particularly advantageous in foamable cosmetic compositions such as a shampoo, shaving product, foam color or foam make up where formation of lather, and the amount of lather and its texture, are perceived as important by consumers. Shampoos, for example, are formulated to achieve a particular texture of lather. Use of the silicone composition according to the invention, especially the silicone composition comprising a hydrophobic organopolysiloxane fluid (A) having a surface tension of from 24 or 27 to 40 mN/m, allows the shampoo formulation to have the same amount and texture of lather, but with the benefit of facilitating rinsing.

One type of fluid organopolysiloxane which is suitable for use as the hydrophobic fluid (A) in a cosmetic composition according to the present invention is a fluid organopolysiloxane containing aryl groups, alternatively phenyl groups, bonded to silicon. Organopolysiloxanes having a phenyl group bonded to substantially all the silicon atoms of the organopolysiloxane are particularly effective. One example of such an organopolysiloxane is a poly(methylphenylsiloxane). A trimethylsiloxy-terminated poly(methylphenylsiloxane), for example, may have a surface tension of 27.1 mN/m. A silanol-terminated poly(methylphenylsiloxane) of similar molecular weight has a surface tension of 33.9 mN/m. Another poly(methylphenylsiloxane), described in Example 1 of WO-2008/152042, has a surface tension of 32.8 mN/m. All of these fluid organopolysiloxanes containing phenyl groups are suitable for use in embodiments of the present invention as hydrophobic fluid (A) of the silicone composition.

An alternative type of fluid organopolysiloxane which is suitable for use as the hydrophobic fluid (A) in the present invention has pendant alkyl substituents having at least 2, alternatively at least 4, alternatively at least 8 carbon atoms, up to 36, alternatively up to 20, alternatively up to 18 carbon atoms. Such alkyl substituents can, for example, be hexyl, octyl, lauryl, tetradecyl, hexadecyl or stearyl substituents. For example, the fluid organopolysiloxane may contain alkyl substituents having 8 to 18 carbon atoms bonded to Si atoms of the organopolysiloxane as well as methyl groups. The fluid organopolysiloxane can, for example, be prepared by reacting poly(methylhydrogensiloxane) or a dimethylsiloxane methylhydrogensiloxane copolymer with one or more alpha-alkene having 8 to 18 carbon atoms, such as a mixture of $C_{12}$ to $C_{14}$ alkenes.

An alternative type of fluid organopolysiloxane which has a surface tension of at least 27 mN/m and which is suitable for use in embodiments of the present invention is a fluid organopolysiloxane containing pendant esterified carboxyalkyl groups. The carboxyalkyl groups can, for example, contain 2 to 12 carbon atoms, particularly 2 to 5 carbon atoms, and can, for example, be carboxymethyl, 2-carboxyethyl, 2-methyl-2-carboxyethyl or 2-ethyl-2-carboxyethyl groups. The carboxyalkyl groups can be esterified by alkyl, aryl, aralkyl or cycloalkyl groups, for example the carboxyalkyl groups can each be esterified by an alkyl group having 1 to 20 carbon atoms. In one embodiment, all or most of the carboxyalkyl groups are esterified by an alkyl group having at least 2, alternatively at least 4, alternatively at least 8 carbon atoms, up to 36, alternatively up to 20, alternatively up to 18 carbon atoms. Examples of suitable alkyl groups having 8 to 18 carbon atoms include n-octyl, 2-ethylhexyl, lauryl, tetradecyl, hexadecyl and stearyl groups. A mixture of different alkyl groups, for example alkyl groups of different chain length, can be used such as a mixture of $C_{12}$ and $C_{14}$ alkyl groups. Such an organopolysiloxane can be prepared by reaction of an organopolysiloxane containing Si—H groups with an ester of an ethylenically unsaturated carboxylic acid, for example a methacrylate or acrylate, in the presence of a hydrosilylation catalyst. The organopolysiloxane containing Si—H groups can, for example, be poly(methylhydrogensiloxane) or a dimethylsiloxane methylhydrogensiloxane copolymer, so that in many cases most or all of the siloxane groups in the organopolysiloxane contain a methyl substituent.

A fluid organopolysiloxane having pendant alkyl substituents having at least 2, alternatively at least 4, alternatively at least 8 carbon atoms, up to 36, alternatively up to 20, alternatively up to 18 carbon atoms, may also contain pendant esterified carboxyalkyl groups. The carboxyalkyl groups can, for example, contain 2 to 12 carbon atoms, particularly 2 to 5 carbon atoms, such as carboxymethyl, 2-carboxyethyl, 2-methyl-2-carboxyethyl or 2-ethyl-2-carboxyethyl groups and may be esterified by alkyl, aryl, aralkyl or cycloalkyl groups, for example alkyl groups having at least 2, alternatively at least 4, alternatively at least 8 carbon atoms, up to 36, alternatively up to 20, alternatively up to 18 carbon atoms, such as n-octyl, 2-ethylhexyl, lauryl, tetradecyl, hexadecyl or stearyl groups or a mixture of $C_{12}$ and $C_{14}$ alkyl groups. A suitable fluid organopolysiloxane (A) can, for example, be prepared by reacting poly(methylhydrogensiloxane) or a dimethylsiloxane methylhydrogensiloxane copolymer with a mixture of one or more alpha-alkene having 8 to 18 carbon atoms and one or more 8-18C alkyl methacrylate or acrylate ester, such as a mixture of $C_{12}$ to $C_{14}$ alkenes and $C_{12}$ to $C_{14}$ alkyl methacrylates. The molar ratio of pendant esterified carboxyalkyl groups to pendant alkyl substituents having 2 to 20 carbon atoms can, for example, be in the range 10:1 to 1:2, with each siloxane unit generally containing a methyl group. A substantially linear polydiorganosiloxane comprising methyl $C_{12-14}$ alkyl siloxane units and methyl 2-methyl-2-carboxyethyl siloxane units in substantially equimolar amounts, in which the carboxyethyl groups are esterified by $C_{12-13}$ alkyl groups has a surface tension of 27.2 mN/m.

An alternative type of fluid organopolysiloxane which is suitable for use as the hydrophobic fluid (A) in the present invention contains aralkyl groups bonded to Si atoms of the organopolysiloxane. The aralkyl group can for example have the formula —X-Ph wherein X denotes a divalent aliphatic organic group bonded to silicon through a carbon atom and Ph denotes an aromatic group. The group X can for example be a divalent alkylene group having from 2 to 10 carbon atoms, for example 2 to 4 carbon atoms, but can alternatively contain an ether linkage between two alkylene groups. Examples of aralkyl groups include benzyl, 2-phenylethyl and 2-phenylpropyl groups. The aralkyl groups can for example be present in diorganosiloxane units such as alkyl aralkyl siloxane units in which the alkyl group has 1 to 4 carbon atoms, for example methyl. The diorganosiloxane units containing an aralkyl group typically comprise 5 to 90%, alternatively 10 to 60%, of the diorganosiloxane units in the hydrophobic organopolysiloxane fluid (A). Other diorganosiloxane units in the hydrophobic organopolysiloxane fluid (A) can for example be dialkylsiloxane units such as dimethylsiloxane units or methyl alkyl siloxane units in which the alkyl group has 2 to 20, alternatively 2 to 4 carbon atoms. The fluid organopolysiloxane (A) can for example be an ethylmethyl, methyl(2-phenylpropyl) siloxane or a dimethyl methyl(2-Phenylpropyl) siloxane.

Mixtures of two or more organopolysiloxanes can be used as the hydrophobic organopolysiloxane fluid (A), for example mixtures of two different types of fluid organopolysiloxane from the types listed above or mixtures of two different organopolysiloxanes of the same type. The hydrophobic organopolysiloxane fluid (A) can be a mixture of a hydrophobic fluid organopolysiloxane with a hydrophobic fluid which is not an organopolysiloxane, provided that the hydrophobic fluid organopolysiloxane comprises at least 50% by weight of the mixture and the hydrophobic fluid which is not an organopolysiloxane is miscible with the hydrophobic fluid organopolysiloxane. The hydrophobic fluid which is not an organopolysiloxane can, for example, be a hydrocarbon fluid such as a liquid polyisobutylene, for example a liquid polyisobutylene having a surface tension of from 30 to 34 mN/m (supplier information).

The silicone composition contains a hydrophobic filler (B) dispersed in the hydrophobic polydiorganosiloxane fluid (A). The hydrophobic filler is generally a particulate material which is solid at 100° C., typically with a surface area as measured by BET measurement of at least 50 m²/g., such as silica, titania, ground quartz, alumina, an aluminosilicate, zinc oxide, magnesium oxide, a salt of an aliphatic carboxylic acids, a reaction product of an isocyanate with an amine, e.g. cyclohexylamine, or an alkyl amide such as ethylenebisstearamide or methylenebisstearamide. Mixtures of two or more of these can be used.

Some of the fillers mentioned above are not hydrophobic in nature, but can be used if made hydrophobic. This can be done either in situ (i.e. when dispersed in the polysiloxane fluid), or by pre-treatment of the filler prior to mixing with the polysiloxane fluid. A preferred filler is silica which is made hydrophobic. Preferred silica materials are those which are prepared by heating, e.g. fumed silica, or by precipitation. The silica filler may, for example, have an average particle size of 0.5 to 50 μm, alternatively 2 to 30 and alternatively 5 to 25 μm. It can be made hydrophobic by treatment with a fatty acid, but is typically made hydrophobic by the use of methyl substituted organosilicon materials such as dimethylsiloxane polymers which are end-blocked with silanol or silicon-bonded alkoxy groups, hexamethyldisilazane, hexamethyldisiloxane or organosilicon resins containing $(CH_3)_3SiO_{1/2}$ groups and silanol groups. Hydrophobing is generally carried out at a temperature of at least 100° C. Mixtures of fillers can be used, for example a highly hydrophobic silica filler or the high surface area fumed silica surface modified with hexamethyldisilazane can be used together with a partially hydrophobic silica.

The amount of hydrophobic filler (B) in the silicone composition can for example be 0.5-50% by weight based on the hydrophobic polydiorganosiloxane fluid (A), alternatively from 1 up to 10 or 15%, alternatively 2 to 9% by weight based on the hydrophobic polydiorganosiloxane fluid (A).

The silicone composition can optionally contain an organosilicon resin in addition to the hydrophobic polydiorganosiloxane fluid (A) and hydrophobic filler (B). The organosilicon resin is generally a non-linear siloxane resin and typically consists of siloxane units of the formula $R'_aSiO_{4-a/2}$ wherein R' denotes a hydroxyl, hydrocarbon or hydrocarbonoxy group, and wherein a has an average value of from 0.5 to 2.4. It typically consists of monovalent trihydrocarbonsiloxy (M) groups of the formula $R''_3SiO_{1/2}$ and tetrafunctional (Q) groups $SiO_{4/2}$ wherein R" denotes a monovalent hydrocarbon group. The number ratio of M groups to Q groups can for example be in the range 0.4:1 to 2.5:1, alternatively 0.5:1 up to 1.1:1 or 0.8:1. A resin comprising M groups, trivalent $R''SiO_{3/2}$ (T) units and Q units can alternatively be used, or up to 20% of units in the organosilicon resin can be divalent units $R''2SiO_{2/2}$. The group R" is typically an alkyl group having 1 to 6 carbon atoms, for example methyl or ethyl, or can be phenyl.

The organosilicon resin, if present, can for example be present in the silicone composition at 1-50% by weight based on the hydrophobic organopolysiloxane fluid (A), alternatively 2-30% wt, alternatively 4-15% wt. The organosilicon resin may be soluble or insoluble in the polysiloxane fluid. If the resin is insoluble in the polysiloxane fluid, the average particle size of the resin may for example be from 0.5 to 400 μm, alternatively 2 to 50 μm.

The silicone composition can optionally contain an organic fluid containing no silicon. Such organic fluids include hydrocarbon fluids such as a liquid polyisobutylene. One type of liquid polyisobutylene has a surface tension of 30.4 mN/m.

Further examples of organic fluids include polyethers in which the repeating ether unit has at least 3 carbon atoms, for example polypropylene oxide, polybutylene oxide or polytetramethylene oxide. One type of polypropylene oxide has a surface tension of 29.0 mN/m.

The organic fluid, if present, can for example be present in the silicone composition at 1-60% by weight based on the hydrophobic organopolysiloxane fluid (A), alternatively 2-50% wt, alternatively 4-25% wt.

Cosmetically active ingredients include emollients, waxes, moisturizers, surface active materials such as surfactants or detergents or emulsifiers, thickeners, water phase stabilizing agents, pH controlling agents, preservatives and cosmetic biocides, sebum absorbants or sebum control agents, vegetable or botanical extracts, vitamins, proteins or amino-acids and their derivatives, pigments, colorants, fillers, conditioning agents, UV absorbers, sunscreen agents, antidandruff agents, antiperspirant agents, deodorant agents, skin protectants, hair dyes, nail care ingredients, fragrances or perfume, antioxidants, oxidizing agents, reducing agents, colour care additives, anticellulites, pearlising agents, chelating agents, film formers, styling agents, anti-acne agents, and mixtures thereof. A wide review of such ingredients may be found in the CTFA cosmetic ingredient handbook.

Cosmetically acceptable medium includes water, solvents, diluents, or mixtures and emulsions thereof.

Examples of emollients include volatile or non-volatile silicone oils; silicone resins such as polypropylsilsesquioxane and phenyl trimethicone; silicone elastomers such as dimethicone crosspolymer; alkylmethylsiloxanes such as $C_{30-45}$ Alkyl Methicone; volatile or non-volatile hydrocarbon compounds, such as squalene, paraffin oils, petrolatum oils and naphthalene oils; hydrogenated or partially hydrogenated polyisobutene; isoeicosane; squalane; isoparaffin; isododecane; isodecane or isohexa-decane; branched $C_8$-$C_{16}$ esters; isohexyl neopentanoate; ester oils such as isononyl isononanoate, cetostearyl octanoate, isopropyl myristate, palmitate derivatives, stearates derivatives, isostearyl isostearate and the heptanoates, octanoates, decanoates or ricinoleates of alcohols or of polyalcohols, or mixtures thereof; hydrocarbon oils of plant origin, such as wheatgerm, sunflower, grapeseed, castor, shea, avocado, olive, soybean, sweet almond, palm, rapeseed, cotton seed, hazelnut, macadamia, jojoba, blackcurrant, evening primrose; or triglycerides of caprylic/capric acids; higher fatty acids, such as oleic acid, linoleic acid or linolenic acid, and mixtures thereof.

Examples of waxes include hydrocarbon waxes such as beeswax, lanolin wax, rice wax, carnauba wax, candelilla wax, microcrystalline waxes, paraffins, ozokerite, polyethylene waxes, synthetic wax, ceresin, lanolin, lanolin derivatives, cocoa butter, shellac wax, bran wax, capok wax, sugar cane wax, montan wax, whale wax, bayberry wax, silicone waxes (e.g. polymethylsiloxane alkyls, alkoxys and/or esters, $C_{30-45}$ alkyldimethylsilyl polypropylsilsesquioxane), and mixtures thereof.

Examples of moisturizers include lower molecular weight aliphatic diols such as propylene glycol and butylene glycol; polyols such as glycerine and sorbitol; and polyoxyethylene polymers such as polyethylene glycol 200; hyaluronic acid and its derivatives, and mixtures thereof.

Examples of surface active materials may be anionic, cationic, amphoteric or nonionic. Nonionic surfactants include dimethicone copolyols, fatty acid esters of polyols, for instance sorbitol or glyceryl mono-, di-, tri- or sesquioleates or stearates, glyceryl or polyethylene glycol laurates; fatty acid esters of polyethylene glycol (polyethylene glycol monostearate such as PEG-50 stearate, PEG-40 monostearate or monolaurate); polyoxyethylenated fatty acid esters (stearate or oleate) of sorbitol; polyoxyethylenated alkyl (lauryl, cetyl, stearyl or octyl)ethers. Further examples of nonionic surfactants include polyoxyalkylene alkyl ethers, for example oxyethylenated and/or oxypropylenated ethers of fatty alcohols such as polyoxyethylene lauryl ethers, ceteareth-30, ethoxylated stearyl alcohols, $C_{12-15}$ pareth-7, oxyethylenated and/or oxypropylenated ethers of glycerol; polyoxyethylene alkylphenol ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, saccharide esters and ethers, such as sucrose stearate, sucrose cocoate and sorbitan stearate, polyoxyalkylene-substituted silicones (rake or ABn types), silicone alkanolamides, silicone esters, silicone glycosides, and mixtures thereof.

Anionic surfactants include carboxylates (sodium 2-(2-hydroxyalkyloxy)acetate)), amino acid derivatives (N-acylglutamates, N-acylgly-cinates or acylsarcosinates), alkyl sulfates, alkyl ether sulfates such as sodium lauryl ether sulphate and oxyethylenated derivatives thereof, sulfonates, isethionates and N-acylisethionates, taurates and N-acyl N-methyltaurates, sulfosuccinates such as disodium PEG-5 citrate lauryl sulphosuccinate and disodium ricinoleamido MEA sulphosuccinate, alkylsulfoacetates, phosphates and alkyl phosphates, polypeptides, anionic derivatives of alkyl polyglycoside (acyl-D-galactoside uronate), and fatty acid soaps, phosphoric esters and salts thereof, such as DEA oleth-10 phosphate; and mixtures thereof.

Cationic surfactants include quaternary ammonium compounds which can be based on dimethylsulphate, diethylsulphate, methylchloride, benzylchloride or epichlorohydrin; primary fatty amine salts, secondary or tertiary, quaternary ammonium salts such as behenyltrimethylammonium chloride, distearyldimethylammonium, cetyltrimethylammonium benzyldimethyl-stearylammonium, palmitylamidopropyltrimethylammonium chloride; and mixtures thereof.

Amphoteric and zwitterionic surfactants include betaines, N-alkylamidobetaines and derivatives thereof, proteins and derivatives thereof, glycine derivatives, sultaines, alkyl polyaminocarboxylates and alkylamphoacetates, and mixtures thereof.

Examples of thickeners include acrylamide copolymers, acrylate copolymers and salts thereof (such as sodium polyacrylate), xanthan gum and derivatives, cellulose gum and cellulose derivatives (such as methylcellulose, methylhydroxypropylcellulose, hydroxypropylcellulose, polypropylhydroxyethylcellulose), starch and starch derivatives (such as hydroxyethylamylose and starch amylase), polyoxyethylene, carbomer, sodium alginate, arabic gum, cassia gum, guar gum and guar gum derivatives, cocamide derivatives, alkyl alcohols, gelatin, PEG-derivatives, saccharides (such as fructose, glucose) and saccharides derivatives (such as PEG-120 methyl glucose diolate), and mixtures thereof.

Examples of pH controlling agents include any water soluble acid such as a carboxylic acid or a mineral acid such as hydrochloric acid, sulphuric acid, and phosphoric acid, monocarboxylic acid such as acetic acid and lactic acid, and polycarboxylic acids such as succinic acid, adipic acid, citric acid, and mixtures thereof.

Examples of preservatives and cosmetic biocides include paraben derivatives, hydantoin derivatives, chlorhexidine and its derivatives, imidazolidinyl urea, phenoxyethanol, silver derivatives, salicylate derivatives, triclosan, ciclopirox olamine, hexamidine, oxyquinoline and its derivatives, PVP-iodine, zinc salts and derivatives such as zinc pyrithione, and mixtures thereof.

Examples of sebum absorbants or sebum control agents include silica silylate, silica dimethyl silylate, dimethicone/vinyl dimethicone crosspolymer, polymethyl methacrylate, cross-linked methylmethacrylate, aluminum starch octenylsuccinate, and mixtures thereof.

Examples of vegetable or botanical extracts are derived from plants (herbs, roots, flowers, fruits, or seeds) in oil or water soluble form, such as coconut, green tea, white tea, black tea, horsetail, ginkgo biloba, sunflower, wheat germ, seaweed, olive, grape, pomegranate, aloe, apricot kernel, apricot, carrot, tomato, tobacco, bean, potato, actzuki bean, catechu, orange, cucumber, avocado, watermelon, banana, lemon or palm. Examples of herbal extracts include dill, horseradish, oats, neem, beet, broccoli, tea, pumpkin, soybean, barley, walnut, flax, ginseng, poppy, avocado, pea, sesame, and mixtures thereof.

Examples of vitamins include a variety of different organic compounds such as alcohols, acids, sterols, and quinones. They may be classified into two solubility groups: lipid-soluble vitamins and water-soluble vitamins. Lipid-soluble vitamins that have utility in personal care formulations include retinol (vitamin A), ergocalciferol (vitamin D2), cholecalciferol (vitamin D3), phytonadione (vitamin K1), and tocopherol (vitamin E). Water-soluble vitamins that have utility in personal care formulations include ascorbic acid (vitamin C), thiamin (vitamin B1), niacin (nicotinic acid), niacinamide (vitamin B3), riboflavin (vitamin B2), pantothenic acid (vitamin B5), biotin, folic acid, pyridoxine (vitamin B6), and cyanocobalamin (vitamin B12). Additional examples of vitamins include derivatives of vitamins such as retinyl palmitate, retinyl acetate, retinyl linoleate, and retinyl propionate, tocopheryl acetate, tocopheryl linoleate, tocopheryl succinate, tocophereth-5, tocophereth-10, tocophereth-12, tocophereth-18, tocophereth-50, PPG-2 tocophereth-5, PPG-5 tocophereth-2, PPG-10 tocophereth-30, PPG-20 tocophereth-50, PPG-30 tocophereth-70, PPG-70 tocophereth-100, sodium tocopheryl phosphate, ascorbyl palmitate, ascorbyl dipalmitate, ascorbyl glucoside, ascorbyl tetraisopalmitate, tetrahexadecyl ascorbate, ascorbyl tocopheryl maleate, potassium ascorbyl tocopheryl phosphate, tocopheryl nicotinate, and mixtures thereof.

Examples of proteins or amino-acids and their derivatives include those extracted from wheat, soy, rice, corn, keratin, elastin or silk. Proteins may be in the hydrolyzed form and they may also be quaternized, such as hydrolyzed elastin, hydrolyzed wheat powder, hydrolyzed silk. Examples of protein include enzymes such as hydrolases, cutinases, oxidases, transferases, reductases, hemicellulases, esterases, isomerases, pectinases, lactases, peroxidases, lactases, catalases, and mixtures thereof. Examples of hydrolases include proteases (bacterial, fungal, acid, neutral or alkaline), amylases (alpha or beta), lipases, mannanases, cellulases, collagenases, lisozymes, superoxide dismutase, and mixtures thereof.

Examples of pigments and colorants include surface treated or untreated iron oxides, surface treated or untreated titanium dioxide, surface treated or untreated mica, silver oxide, silicates, chromium oxides, carotenoids, carbon black, ultramarines, chlorophyllin derivatives and yellow ocher. Surface treatments include silicon based compound and fluoro based compounds. Examples of organic pigments include aromatic types including azo, indigoid, triphenylmethane, anthraquinone, and xanthine dyes which are designated as D&C and FD&C blues, browns, greens, oranges, reds, yellows, etc, and mixtures thereof.

Examples of cosmetically active fillers include talc, micas, kaolin, zinc or titanium oxides, calcium or magnesium carbonates, silica, silica silylate, titanium dioxide, glass or ceramic beads, polymethylmethacrylate beads, boron nitride, aluminum silicate, aluminum starch octenylsuccinate, bentonite, magnesium aluminum silicate, nylon, silk powder metal soaps derived from carboxylic acids having 8-22 carbon atoms, non-expanded synthetic polymer powders, expanded powders and powders from natural organic compounds, such as cereal starches, which may or may not be crosslinked, copolymer microspheres, polytrap, silicone resin microbeads, and mixtures thereof. The fillers may be surface treated to modify affinity or compatibility with remaining ingredients.

Examples of conditioning agents include silicone conditioning agents, cationic conditioning agents and hydrophobic conditioning agents. Silicone conditioning agents include silicone oils such as dimethicone; silicone gums such as dimethiconol; silicone resins such as trimethylsiloxy silicate, polypropyl silsesquioxane; silicone elastomers; alkylmethylsiloxanes; organomodified silicone oils, such as amodimethicone, aminopropyl phenyl trimethicone, phenyl trimethicone, trimethyl pentaphenyl trisiloxane, silicone quaternium-16/glycidoxy dimethicone crosspolymer, silicone quaternium-16; saccharide functional siloxanes; carbinol functional siloxanes; silicone polyethers; siloxane copolymers (divinyldimethicone/dimethicone copolymer); acrylate or acrylic functional siloxanes; and mixtures or emulsions thereof.

Examples of cationic conditioning agents include guar derivatives such as hydroxypropyltrimethylammonium derivative of guar gum; cationic cellulose derivatives, cationic starch derivatives; quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polymeric quaternary ammonium salts of hydroxyethyl cellulose reacted with a fatty alkyl dimethyl ammonium substituted epoxide; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats Polyquaternium-7, Polyquaternium-8, Polyquaternium-10, Polyquaternium-11, and Polyquaternium-23. Other categories of conditioners include cationic surfactants such as cetyl trimethylammonium chloride, cetyl trimethylammonium bromide, stearyltrimethylammonium chloride, and mixtures thereof. In some instances, the cationic conditioning agent is also hydrophobically modified, such as hydrophobically modified quaternized hydroxyethylcellulose polymers; cationic hydrophobically modified galactomannan ether; and mixtures thereof.

Examples of hydrophobic conditioning agents include guar derivatives; galactomannan gum derivatives; cellulose derivatives; and mixtures thereof.

UV absorbers and sunscreen agents include those which absorb ultraviolet light between about 290-320 nanometers (the UV-B region) and those which absorb ultraviolet light in the range of 320-400 nanometers (the UV-A region).

Some examples of sunscreen agents are aminobenzoic acid, cinoxate, diethanolamine methoxycinnamate, digalloyl trioleate, dioxybenzone, ethyl 4-[bis(Hydroxypropyl)] aminobenzoate, glyceryl aminobenzoate, homosalate, lawsone with dihydroxyacetone, menthyl anthranilate, octocrylene, ethyl hexyl methoxycinnamate, octyl salicylate, oxybenzone, padimate O, phenylbenzimidazole sulfonic acid, red petrolatum, sulisobenzone, titanium dioxide, trolamine salicylate, and mixtures thereof.

Some examples of UV absorbers are acetaminosalol, allatoin PABA, benzalphthalide, benzophenone, benzophenone 1-12, 3-benzylidene camphor, benzylidenecamphore hydrolyzed collagen sulfonamide, benzylidene camphor sulfonic Acid, benzyl salicylate, bornelone, bumetriozole, butyl Methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium distyrylbiphenyl triaminotriazine stilbenedisulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, ethyl hexyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, triPABA panthenol, urocanic acid, VA/crotonates/methacryloxybenzophenone-1 copolymer, and mixtures thereof.

Examples of antidandruff agents include pyridinethione salts, selenium compounds such as selenium disulfide, and soluble antidandruff agents, and mixtures thereof.

Examples of antiperspirant agents and deodorant agents include aluminum chloride, aluminum zirconium tetrachlorohydrex GLY, aluminum zirconium tetrachlorohydrex PEG, aluminum chlorohydrex, aluminum zirconium tetrachlorohydrex PG, aluminum chlorohydrex PEG, aluminum zirconium trichlorohydrate, aluminum chlorohydrex PG, aluminum zirconium trichlorohydrex GLY, hexachlorophene, benzalkonium chloride, aluminum sesquichlorohydrate, sodium bicarbonate, aluminum sesquichlorohydrex PEG, chlorophyllin-copper complex, triclosan, aluminum zirconium octachlorohydrate, zinc ricinoleate, and mixtures thereof.

Examples of skin protectants include allantoin, aluminum acetate, aluminum hydroxide, aluminum sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, zinc oxide, and mixtures thereof.

Examples of hair dyes include 1-acetoxy-2-methylnaphthalene; acid dyes; 5-amino-4-chloro-o-cresol; 5-amino-2,6-dimethoxy-3-hydroxypyridine; 3-amino-2,6-dimethylphenol; 2-amino-5-ethylphenol HCl; 5-amino-4-fluoro-2- methylphenol sulfate; 2-amino-4-hydroxyethylaminoanisole; 2-amino-4-hydroxyethylaminoanisole sulfate; 2-amino-5-nitrophenol; 4-amino-2-nitrophenol; 4-amino-3-nitrophenol; 2-amino-4-nitrophenol sulfate; 4-aminophenol HCl; p-aminophenol HCl; m-aminophenol; o-aminophenol; 4,6-bis(2-hydroxyethoxy)-m-phenylenediamine HCl; 2,6-bis(2-hydroxyethoxy)-3,5-pyridinediamine HCl; 2-chloro-6-ethylamino-4-nitrophenol; 2-chloro-5-nitro-N-hydroxyethyl p-phenylenediamine; 2-chloro-p-phenylenediamine; 3,4-diaminobenzoic acid; 4,5-diamino-1-((4-chlorophenyl)methyl)-1H-pyrazole-sulfate; 2,3-diaminodihydropyrazolo pyrazolone dimethosulfonate; 2,6-diaminopyridine; 2,6-diamino-3-((pyridin-3-yl)azo)pyridine; dihydroxyindole; dihydroxyindoline; N,N-dimethyl-p-phenylenediamine; 2,6-dimethyl-p-phenylenediamine; N,N-dimethyl-p-phenylenediamine sulfate; direct dyes; 4-ethoxy-m-phenylenediamine sulfate; 3-ethylamino-p-cresol sulfate; N-ethyl-3-nitro PABA; gluconamidopropyl aminopropyl dimethicone; Haematoxylon brasiletto wood extract; HC dyes; Lawsonia inermis (Henna) extract; hydroxyethyl-3,4-methylenedioxyaniline HCl; hydroxyethyl-2-nitro-p-toluidine; hydroxyethyl-p-phenylenediamine sulfate; 2-hydroxyethyl picramic acid; hydroxypyridinone; hydroxysuccinimidyl C21-22 isoalkyl acidate; isatin; Isatis tinctoria leaf powder; 2-methoxymethyl-p-phenylenediamine sulfate; 2-methoxy-p-phenylenediamine sulfate; 6-methoxy-2,3-pyridinediamine HCl; 4-methylbenzyl 4,5-diamino pyrazole sulfate; 2,2'-methylenebis 4-aminophenol; 2,2'-methylenebis-4-aminophenol HCl; 3,4-methylenedioxyaniline; 2-methylresorcinol; methylrosanilinium chloride; 1,5-naphthalenediol; 1,7-naphthalenediol; 3-nitro-p-Cresol; 2-nitro-5-glyceryl methylaniline; 4-nitroguaiacol; 3-nitro-p-hydroxyethylaminophenol; 2-nitro-N-hydroxyethyl-p-anisidine; nitrophenol; 4-nitrophenyl aminoethylurea; 4-nitro-o-phenylenediamine dihydrochloride; 2-nitro-p-phenylenediamine dihydrochloride; 4-nitro-o-phenylenediamine HCl; 4-nitro-m-phenylenediamine; 4-nitro-o-phenylenediamine; 2-nitro-p-phenylenediamine; 4-nitro-m-phenylenediamine sulfate; 4-nitro-o-phenylenediamine sulfate; 2-nitro-p-phenylenediamine sulfate; 6-nitro-2,5-pyridinediamine; 6-nitro-o-toluidine; PEG-3 2,2'-di-p-phenylenediamine; p-phenylenediamine HCl; p-phenylenediamine sulfate; phenyl methyl pyrazolone; N-phenyl-p-phenylenediamine HCl; pigment blue 15:1; pigment violet 23; pigment yellow 13; pyrocatechol; pyrogallol; resorcinol; sodium picramate; sodium sulfanilate; solvent yellow 85; solvent yellow 172; tetraaminopyrimidine sulfate; tetrabromophenol blue; 2,5,6-triamino-4-pyrimidinol sulfate; and 1,2,4-trihydroxybenzene.

Examples of nail care ingredients include butyl acetate; ethyl acetate; nitrocellulose; acetyl tributyl citrate; isopropyl alcohol; adipic acid/neopentyl glycol/trimelitic anhydride copolymer; stearalkonium bentonite; acrylates copolymer; calcium pantothenate; Cetraria islandica extract; Chondrus crispus; styrene/acrylates copolymer; trimethylpentanediyl dibenzoate-1; polyvinyl butyral; N-butyl alcohol; propylene glycol; butylene glycol; mica; silica; tin oxide; calcium borosilicate; synthetic fluorphlogopite; polyethylene terephtalate; sorbitan laurate derivatives; talc; jojoba extract; diamond powder; isobutylphenoxy epoxy resin; silk powder; and mixtures thereof.

Examples of fragrances or perfumes include hexyl cinnamic aldehyde; anisaldehyde; methyl-2-n-hexyl-3-oxo-cyclopentane carboxylate; dodecalactone gamma; methylphenylcarbinyl acetate; 4-acetyl-6-tert-butyl-1,1-dimethyl indane; patchouli; olibanum resinoid; labdanum; vetivert; copaiba balsam; fir balsam; 4-(4-hydroxy-4-methyl pentyl)-3-cyclohexene-1-carboxaldehyde; methyl anthranilate; geraniol; geranyl acetate; linalool; citronellol; terpinyl acetate; benzyl salicylate; 2-methyl-3-(p-isopropylphenyl)-propanal; phenoxyethyl isobutyrate; cedryl acetal; aubepine; musk fragrances; macrocyclic ketones; macrolactone musk fragrances; ethylene brassylate; and mixtures thereof. Further perfume ingredients are described in detail in standard textbook references such as *Perfume and Flavour Chemicals,* 1969, S. Arctander, Montclair, N.J.

Examples of antioxidants include acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, Camellia sinensis Oil, chitosan ascorbate, chitosan glycolate, chitosan salicylate, chlorogenic acids, cysteine, cysteine HCl, decyl mercaptomethylimidazole, erythorbic acid, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (Melaleuca aftemifolia) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl-biguanide, tris(nonylphenyl) phosphite, ubiquinone, zinc dibutyldithiocarbamate, and mixtures thereof.

Examples of oxidizing agents include ammonium persulfate, calcium peroxide, hydrogen peroxide, magnesium peroxide, melamine peroxide, potassium bromate, potassium caroate, potassium chlorate, potassium persulfate, sodium bromate, sodium carbonate peroxide, sodium chlorate, sodium iodate, sodium perborate, sodium persulfate, strontium dioxide, strontium peroxide, urea peroxide, zinc peroxide, and mixtures thereof.

Examples of reducing agents include ammonium bisufite, ammonium sulfite, ammonium thioglycolate, ammonium thiolactate, cystemaine HCl, cystein, cysteine HCl, ethanolamine thioglycolate, glutathione, glyceryl thioglycolate, glyceryl thioprionate, hydroquinone, p-hydroxyanisole, isooctyl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, superoxide dismutase, thioglycerin, thioglycolic acid, thiolactic acid, thiosalicylic acid, zinc formaldehyde sulfoxylate, and mixtures thereof.

Examples of antiacne agents include salicylic acid, sulfur benzoyl, peroxide, tretinoin, and mixtures thereof.

Examples of cosmetically acceptable diluents include silicon containing diluents such as hexamethyldisiloxane, octamethyltrisiloxane, and other short chain linear siloxanes such as octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, cyclic siloxanes such as decamethylcyclopentasiloxane or dodecamethylcyclohexasiloxane; organic diluents such as butyl acetate, alkanes, alcohols, ketones, esters, ethers, glycols, glycol ethers, hydrofluorocarbons or any other material which can dilute the formulation without adversely affecting any of the component materials of the cosmetic composition. Alkanes include isododecane, isohexadecane, Isopar L ($C_{11}$-$C_{13}$), Isopar H ($C_{11}$-$C_{12}$), and hydrogenated polydecene. Ethers and esters include isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic diluents include fats, oils, fatty acids, and fatty alcohols.

When preparing a cosmetic composition according to the invention, the finely divided solid hydrophobic filler (B) is dispersed in the hydrophobic organopolysiloxane fluid (A) before the solid hydrophobic filler (B) or the hydrophobic organopolysiloxane fluid (A) is mixed with the remaining ingredients of the cosmetic composition. The effect as a rinsing aid of the silicone composition comprising hydrophobic organopolysiloxane fluid (A) and solid hydrophobic filler (B) is much greater if the hydrophobic organopolysiloxane fluid (A) and solid hydrophobic filler (B) are pre-mixed to form the silicone composition compared to adding the hydrophobic organopolysiloxane fluid (A) and the solid hydrophobic filler (B) separately to the cosmetic composition.

If an organosilicon resin is used as part of the silicone composition, the organosilicon resin is also usually pre-mixed with the hydrophobic organopolysiloxane fluid (A) and solid hydrophobic filler (B) before mixing with the other ingredients of the cosmetic composition.

A method of producing a cosmetic composition is included comprising (i) preparing a silicone composition by dispersing a finely divided solid hydrophobic filler in a hydrophobic organopolysiloxane fluid having a surface tension of from 15 to 40 mN/m and (ii) mixing the resulting silicone composition with a cosmetically active ingredient in a cosmetically acceptable medium to produce the cosmetic composition.

The silicone composition comprising hydrophobic organopolysiloxane fluid (A) and solid hydrophobic filler (B) can be mixed directly with a cosmetic composition or with one or more of the ingredients of the cosmetic composition, or can be added in solution, for example in one of the cosmetically acceptable diluents described above such as an alkane, or can be added in emulsion form. The silicone composition can for example be added as an oil-in-water emulsion stabilised by a nonionic, anionic, cationic, amphoteric or zwitterionic surfactant. The surfactants described above for use in the cosmetic composition are generally suitable for emulsifying the silicone composition in water, for example nonionic surfactants such as polyoxyalkylene alkyl ethers, fatty acid esters of polyethylene glycol, oxyethylenated and/or oxypropylenated ethers of glycerol, polyoxyethylenated fatty acid esters of sorbitol, polyoxyethylene alkylphenol ethers, or polyoxyethylene sorbitan alkyl esters.

The silicone composition comprising the hydrophobic organopolysiloxane fluid (A) and solid hydrophobic filler (B) is incorporated at 0.001% to 5% by weight of the cosmetic composition, for example at least 0.01 up to 2% by weight, or at least 0.05 up to 1% by weight, or 0.05 to 0.5% by weight of the cosmetic composition. This is a lower level than conventional silicone additives such as silicone conditioning agents. Even at these low levels sensory benefits can be identified, such as improved smoothness of hair or skin treated with a cosmetic composition according to the invention compared to a cosmetic composition which does not contain the silicone composition comprising hydrophobic organopolysiloxane fluid (A) and solid hydrophobic filler (B). As well as being smoother, hair treated with a cosmetic composition according to the invention such as a shampoo, conditioning composition or colouring product can be easier to comb than the same composition which does not contain the silicone composition.

The present cosmetic composition comprising the hydrophobic organopolysiloxane fluid (A) and solid hydrophobic filler (B) is used to facilitate rinsing of a shampoo, shower gel, shaving product, personal washing product, mouth wash, face wash, foam color, foam make up or exfoliating product from a substrate when incorporated in such shampoo, shower gel, shaving product, personal washing product, mouth wash, face wash, foam color, foam make up or exfoliating product containing a surfactant, such as a detersive surfactant.

Also included is a method of facilitating rinsing of a cosmetic composition from hair or skin, wherein a silicone composition comprising (A) a hydrophobic organopolysiloxane fluid having a surface tension of from 15 to 40 mN/m and (B) a finely divided solid hydrophobic filler dispersed in the organopolysiloxane fluid (A) is incorporated in the cosmetic composition.

Methods to measure the impact on the rinsing stage include the measurement of the time needed to remove all or part of the lather or foam up to a certain defined level, or the count of buckets or recipients or amounts (in liters or grams) of water necessary to remove all or part of the lather or foam up to a certain defined level. The positive impact on the rinsing stage may be a reduction of time of use of running water, or a reduced number of buckets of water, or a reduced amount of water (in terms of buckets or liters or grams).

The cosmetic compositions may be used by the standard methods, such as applying them to the human or animal body, e.g. skin or hair, using applicators, brushes, applying by hand, pouring them and/or possibly rubbing or massaging the composition onto or into the body. Removal methods, for example for colour cosmetics are also well known standard methods, including washing, wiping, peeling and the like.

The cosmetic compositions are applied topically to the desired area of the skin or hair in an amount sufficient to provide a satisfactory cleansing or conditioning of the skin or hair. The compositions may be diluted with water prior to, during, or after topical application, and then subsequently rinsed or wiped off of the applied surface, for example rinsed off of the applied surface using water or a water-insoluble substrate in combination with water.

The cosmetic compositions may be used on hair in a conventional manner. An effective amount of the composition for washing or conditioning hair is applied to the hair. Such effective amounts generally range from 1 g to 50 g, alternatively from 1 g to 20 g. Application to the hair typically includes working the cosmetic composition through the hair such that most or all of the hair is contacted with the cosmetic composition. These steps can be repeated as many times as desired to achieve the desired benefit.

Benefits obtained from using the cosmetic compositions on hair include one or more of the following benefits: color retention, improvement in coloration process, hair conditioning, softness, detangling ease, silicone deposition, anti-static, anti-frizz, lubricity, shine, strengthening, viscosity, tactile, wet combing, dry combing, straightening, heat protection, styling, or curl retention.

Hair treated with a shampoo, conditioning composition or colouring product according to the invention may also be perceived as having more volume than hair treated with a similar shampoo, conditioning composition or colouring product which does not contain the silicone composition of the invention.

Also included is a method of facilitating combing of hair, wherein a silicone composition comprising (A) a hydrophobic organopolysiloxane fluid having a surface tension of from 15 to 40 mN/m and (B) a finely divided solid hydrophobic filler dispersed in the organopolysiloxane fluid (A) is incorporated in a shampoo, conditioning composition or colouring product which is applied to the hair and rinsed from the hair.

The cosmetic compositions may be used on skin in a conventional manner. An effective amount of the composition for the purpose is applied to the skin. Such effective amounts generally range from 1 mg/cm2 to 3 mg/cm2. Application to the skin typically includes working the cosmetic composition into the skin. This method for applying to the skin comprises the steps of contacting the skin with the cosmetic composition in an effective amount and then rubbing the composition into the skin. These steps can be repeated as many times as desired to achieve the desired benefit.

Benefits obtained from using the cosmetic compositions on skin include one or more of the following benefits: skin softness, suppleness, moisturisation, skin feel, foam generation.

Also included is a method of increasing the smoothness, silkiness and/or shine of hair, wherein a silicone composition comprising (A) a hydrophobic organopolysiloxane fluid having a surface tension of from 15 to 40 mN/m and (B) a finely divided solid hydrophobic filler dispersed in the organopolysiloxane fluid (A) is incorporated in a shampoo, conditioning composition or colouring product which is applied to the hair and rinsed from the hair.

The cosmetic composition may be used to care for keratinous substrates, that is to cleanse, to condition, to refresh, to make up, to remove make up, to fix hair.

EXAMPLES

The invention is illustrated by the following Examples, in which parts and percentages are by weight.

Example 1

91 g dimethyl methyl(2-phenylpropyl) siloxane fluid, having a surface tension of 28.0 mN/m, was mixed with 6 g high surface area fumed silica surface modified with hexamethyldisilazane (Cab-O-Sil® TS530) and 3 g partially hydrophobic silica (Aerosil® R972) at 3500 rpm for 80 seconds, followed by mixing at 6000 rpm with homogeniser for 60 seconds to form a silicone composition.

10 g of the silicone composition was mixed with 0.98 g ethoxylated stearyl alcohol (Volpo™ S2) and 0.98 g ethoxylated stearyl alcohol (Volpo™ S20) and heated at 70° C. for 10 minutes, then mixed over 5 minutes at 3500 rpm with gradual addition of 15.7 g of a 4% aqueous thickener solution and 22.53 g more water to form a 20% by weight aqueous emulsion of the silicone composition.

The aqueous emulsion of the silicone composition was added at 0.4% by weight to each of 3 commercial shampoos—'Pantene Classic Care', 'Garnier Ultra-Doux' and 'Syoss', providing for an amount of 0.08% by weight silicone composition based on the shampoo. Shake tests (I) were carried out to assess the effectiveness of the silicone composition as a rinse aid. Comparison tests were made using each shampoo without added silicone composition.

In the shake tests (I), each shampoo was first diluted to 0.5% with deionised water to form a foamable solution simulating washing with the shampoo (above the Critical Micelle Concentration of the detersive surfactant). In parallel, each shampoo was diluted to 0.05% with deionised water to form a foamable solution simulating the rinsing step when using the shampoo (below the Critical Micelle Concentration of the detersive surfactant). 100 ml of each foamable solution simulating the wash step and that simulating the rinse step was taken into a clean 250 ml jar which had the liquid level was marked as 0 and the upper limit of the jar was marked as 100. The jar was shaken for 60 seconds. After each shaking cycle the initial foam height was recorded as a percentage of available free volume. The foamed solution was allowed to stand for 2 minutes (collapse time) and the percentage of foam was recorded. The results are shown in Tables 1, 2 and 3.

Examples 2 to 6

Example 1 was repeated replacing the dimethyl methyl (2-Phenylpropyl) siloxane fluid of Example 1 by the following:

Example 2: a mixture of 50% trimethylsiloxy-terminated poly(methylphenylsiloxane) having a surface tension of 27.1 mN/m with 50% liquid polyisobutylene (Dynapak® poly 55) having a surface tension of 30.4 mN/m;

Example 3: a mixture of 50% dimethyl methyl(2-Phenylpropyl) siloxane fluid ($\gamma$=28.0 mN/m), as used in Example 1 with 50% liquid polyisobutylene (Dynapak® poly 55) ($\gamma$=30.4 mN/m);

Example 4: linear fluid polydimethylsiloxane with randomly distributed $C_{12-14}$ alkyl chains having a surface tension of 28.0 mN/m;

Example 5: a mixture of 50% linear polydimethylsiloxane with randomly distributed $C_{12-14}$ alkyl chains ($\gamma$=28.0 mN/m) with 50% liquid polyisobutylene (Dynapak® poly 55) ($\gamma$=30.4 mN/m);

Example 6: a mixture of 50% fluid polymethylalkylsiloxane having $C_{12-14}$ alkyl groups having a surface tension of 31 mN/m with 50% liquid polyisobutylene (Dynapak® poly 55) ($\gamma$=30.4 mN/m).

The results of the shake tests for Examples 1 to 6 are shown in Tables 1 to 3, each Table showing the results for a particular commercial shampoo.

TABLE 1

| Shampoo | WASH | | RINSE | |
| --- | --- | --- | --- | --- |
| | Wash foam height | Foam height after 2 min | Rinse foam height | Foam height after 2 min |
| Pantene no additive | 100% | 100% | 70% | 60% |
| Pantene-Example 1 | 80% | 70% | 10% | 5% |
| Pantene-Example 2 | 80% | 70% | 20% | 10% |
| Pantene-Example 3 | 80% | 80% | 10% | 10% |
| Pantene-Example 4 | 50% | 50% | 10% | 0% |
| Pantene-Example 5 | 80% | 70% | 20% | 10% |
| Pantene-Example 6 | 80% | 60% | 20% | 20% |

TABLE 2

| Shampoo | WASH | | RINSE | |
| --- | --- | --- | --- | --- |
| | Wash foam height | Foam height after 2 min | Rinse foam height | Foam height after 2 min |
| Ultra-Doux no additive | 100% | 100% | 100% | 100% |
| Ultra-Doux-Example 1 | 70% | 60% | 10% | 5% |
| Ultra-Doux-Example 2 | 80% | 70% | 10% | 10% |
| Ultra-Doux-Example 3 | 70% | 60% | 5% | 0% |
| Ultra-Doux-Example 4 | 50% | 40% | 5% | 0% |
| Ultra-Doux-Example 5 | 60% | 60% | 10% | 5% |
| Ultra-Doux-Example 6 | 70% | 60% | 20% | 20% |

TABLE 3

| Shampoo | WASH | | RINSE | |
| --- | --- | --- | --- | --- |
| | Wash foam height | Foam height after 2 min | Rinse foam height | Foam height after 2 min |
| Syoss no additive | 100% | 100% | 60% | 50% |
| Syoss 5 g/l-Example 1 | 70% | 60% | 20% | 5% |
| Syoss 5 g/l-Example 2 | 80% | 60% | 20% | 20% |
| Syoss 5 g/l-Example 3 | 80% | 70% | 10% | 5% |
| Syoss 5 g/l-Example 4 | 60% | 50% | 10% | 0% |
| Syoss 5 g/l-Example 5 | 60% | 50% | 10% | 5% |
| Syoss 5 g/l-Example 6 | 80% | 60% | 20% | 10% |

As can be seen from Tables 1 to 3, the commercial shampoos all formed considerable amounts of foam even at the concentration simulating the rinsing step. Addition of a silicone composition according to the invention showed only a small reduction in lather at the wash concentration, but a drastic and significant reduction in foam at the concentration simulating the rinsing step.

Example 7

A 20% by weight aqueous emulsion of a silicone composition was prepared by the method described in Example 1 replacing the dimethyl methyl(2-Phenylpropyl) siloxane fluid of Example 1 by a mixture of 50% methyl($C_{12-14}$ alkyl)siloxane methyl(2-methyl-2-carboxyethyl)siloxane copolymer, in which the carboxyl groups are esterified with $C_{12-13}$ alkyl groups, sold under the trade mark 'Dow Corning® SF-8422' and having a surface tension of 27.2 mN/m, with 50% 'Dynapak® poly 55' liquid polyisobutylene ($\gamma$=30.4 mN/m).

Shampoo compositions were prepared by adding 500 µl of the silicone emulsion to 50 g of each of 'Pantene' and 'Ultra-Doux' shampoos. The resulting shampoo compositions were used in foam tests on hair. Pre-washed tresses of hair (5 tresses for each test) were wetted with tap water at 37° C. for 30 seconds, then shampooed with 5 g of the shampoo composition, stroking the tresses downward for 30 seconds to form a lather. Excess lather was removed by stroking the tresses 3 times between two fingers. Each tress was then rinsed by dipping in tap water at 37° C. for 5 seconds and removing excess water by stroking the tresses between two fingers. The excess water was collected and photographed to observe the amount of foam on the rinse water. This rinsing procedure was repeated two more times. Comparison tests were made using each shampoo without added silicone composition. The amounts of foam are listed in Table 4 below which shows the percentage of the water surface covered by foam.

TABLE 4

| | Foam after 1 rinse | Foam after 2 rinses | Foam after 3 rinses |
| --- | --- | --- | --- |
| Pantene-no additive | 100% | 20% | 0% |
| Pantene-Example 7 | 100% | 5% | 0% |
| Ultra-Doux-no additive | 100% | 90% | 40% |
| Ultra-Doux-Example 7 | 100% | 50% | 10% |

It can be seen from Table 4 that the silicone composition of Example 7 did not inhibit lathering in the wash, but aided the speed of removal of foam by rinsing for each of the commercial shampoos tested.

Examples 8 to 11

A 20% by weight aqueous emulsion of a silicone composition was prepared by the method described in Example 1 replacing the dimethyl methyl(2-Phenylpropyl) siloxane fluid of Example 1 by the following Example 8: trimethylsiloxy-terminated poly(methylphenylsiloxane) fluid having a surface tension of 32.0 mN/m;

Example 9: polymethylalkylsiloxane having $C_{12-14}$ alkyl groups having a surface tension of 31.0 mN/m;

Example 10: a mixture of 50% trimethylsiloxy-terminated poly(methylphenylsiloxane) fluid ($\gamma$=32.0 mN/m) with 50% liquid polyisobutylene (Dynapak® poly 55) ($\gamma$=30.4 mN/m);

Example 11: a mixture of 50% polymethylalkylsiloxane having $C_{12-14}$ alkyl groups ($\gamma$=31.0 mN/m) with 50% liquid polyisobutylene (Dynapak® poly 55) ($\gamma$=30.4 mN/m).

Each aqueous emulsion of the silicone composition was added at 0.5% by weight (0.1% by weight silicone composition based on shampoo) to a commercial shampoo (Pantene). The resulting shampoo compositions were used in sensory tests on hair. Pre-washed tresses of hair (2 tresses for each test) were wetted with tap water at 37° C. for 30 seconds, then shampooed with 5 g of the shampoo composition, stroking the tresses downward for 30 seconds to form a lather. Excess lather was removed by stroking the tresses 3 times between two fingers. Each tress was then rinsed by dipping in tap water at 37° C. for 30 seconds and removing excess water by stroking the tresses between two fingers. The resulting washed and rinsed tresses were each assessed by 5 qualified panelists evaluating the following parameters: smoothness, silkiness, shine, ease of combing. Comparison tests were made using the shampoo without added silicone composition.

Hair tresses treated with the shampoos of Examples 8 and 9 were smoother and easier to comb than the control without added silicone composition. The panelists could feel the presence of a film on the hair but the hair tresses were not perceived to be greasy nor harsh. Hair tresses treated with the shampoos of Examples 10 and 11 were smoother and had more volume than the control without added silicone composition, but no advantage or disadvantage was perceived for the combing in these Examples. The panelists could also feel the presence of a film but the hair tresses were not perceived to be greasy nor harsh.

Example 12

90 g dimethyl methyl(2-phenylpropyl) siloxane fluid ($\gamma$=28.0 mN/m) was mixed with 4 g high surface area fumed silica surface modified with hexamethyldisilazane (Cab-O-Sil® TS530) and 1 g partially hydrophobic silica (Aerosil® R972) at 3500 rpm for 80 seconds, followed by mixing at 6000 rpm with homogeniser for 60 seconds to form a silicone composition.

The silicone composition was added at 1% by weight to a commercial shampoo—'Garnier Ultra-Doux'.

Shake tests (II) were carried out to assess the effectiveness of the silicone composition as a rinse aid. Comparison tests were made using the shampoo without added silicone composition.

In the shake tests (II), the shampoo with or without added silicone composition was first diluted to 0.5% with deionised water to form a foamable solution simulating washing with the shampoo (above the Critical Micelle Concentration of the detersive surfactant). 100 ml of each foamable solution simulating the wash step taken into a clean 250 ml jar which had the liquid level was marked as 0 and the upper limit of the jar was marked as 100. Five hair tresses were clamped into the cap of the jar so that they soak into the shampoo solution. The jar was shaken for 60 seconds. After each shaking cycle the initial foam height was recorded as a percentage of available free volume. The hair tresses were then removed from the jar and squeezed until only 10 ml (10 gm) of the foamable solution remain on the hair. The tresses were then added to a jar containing 100 ml of fresh water and the jar was shaken for 60 seconds. The foam height was recorded and the hair tresses were again removed from the jar and transferred to a jar with fresh water. The operation was repeated until no foam appears anymore after shaking. The number of operations necessary to reach that point is recorded as the number of rinses necessary to obtain clear water.

The results indicate that the addition of the silicone composition to the shampoo allowed for reducing the number of rinses from 5 to 3 with a moderate impact on the foamability of the shampoo. The sensory properties of the hair were not affected by the reduction of the rinses, as assessed by 5 panelists with regard to ease of combing, smoothness, alignment and volume.

TABLE 5

| Foam height | Commercial shampoo (Ultra Doux) | Example 12: Commercial shampoo (Ultra Doux) + silicone composition |
|---|---|---|
| Wash | 100 | 80 |
| Rinse n°1 | 40 | 20 |
| Rinse n°2 | 10 | 2.5 |
| Rinse n°3 | 5 | 0 |
| Rinse n°4 | 2.5 | 0 |
| Rinse n°5 | 0 | 0 |

The invention claimed is:

1. A cosmetic composition for application to a keratinous substrate of a human, said cosmetic composition comprising:
   a cosmetically active ingredient in a cosmetically acceptable medium; and
   a silicone composition comprising;
   (A) a hydrophobic organopolysiloxane fluid having a surface tension of from 15 to 40 mN/m, and
   (B) a finely divided solid hydrophobic filler dispersed in the organopolysiloxane fluid (A);
   wherein the cosmetic composition is a foamable composition such that a foam or lather forms during application to and/or use on a keratinous substrate.

2. The cosmetic composition according to claim 1, wherein the organopolysiloxane fluid (A) has a surface tension ≥27 mN/m and <40 mN/m.

3. The cosmetic composition according to claim 1, wherein the organopolysiloxane fluid (A) contains aryl or aralkyl groups bonded to Si atoms of the organopolysiloxane.

4. The cosmetic composition according to claim 3, wherein the organopolysiloxane fluid (A) contains phenyl groups bonded to Si atoms of the organopolysiloxane.

5. The cosmetic composition according to claim 1, wherein the organopolysiloxane fluid (A) contains alkyl substituents having 4 to 36 carbon atoms bonded to Si atoms of the organopolysiloxane.

6. The cosmetic composition according to claim 1, wherein the organopolysiloxane fluid (A) contains carboxyalkyl groups esterified by an alkyl group having 4 to 36 carbon atoms.

7. The cosmetic composition according to claim 1, wherein the finely divided solid hydrophobic filler (B) is present at 1 to 15% by weight based on the organopolysiloxane fluid (A).

8. The cosmetic composition according to claim 1, wherein the silicone composition is present at 0.001% to 2% by weight of the cosmetic composition.

9. The cosmetic composition according to claim 1, wherein the silicone composition is present as an oil-in-water emulsion.

10. The cosmetic composition according to claim 1, wherein the cosmetic composition is selected from a shampoo, shower gel, shaving product, personal washing product, mouth wash, face wash, foam color, foam make up or exfoliating product and the cosmetically active ingredient comprises a surfactant.

11. The cosmetic composition according to claim 10, wherein the cosmetic composition is a shampoo for application to human hair.

12. The cosmetic composition according to claim 10, wherein the cosmetic composition is selected from a face wash, a foam color, or a foam make up for application to human skin or hair.

13. The cosmetic composition according to claim 1, wherein the cosmetically active ingredient comprises an emollient, humectant, pH adjusting agent, chelating agent, conditioning agent or exfoliating agent.

14. A method of facilitating rinsing of a cosmetic composition from human hair or skin, said method comprising:
   incorporating a silicone composition in a composition to form the cosmetic composition;
   applying the cosmetic composition to human hair or skin; and
   rinsing the cosmetic composition from the human hair or skin;

wherein the silicone and cosmetic compositions are according to claim 1.

15. A method of facilitating combing of human hair, said method comprising:
  incorporating a silicone composition in a shampoo, conditioning composition, or colouring product to form a cosmetic composition;
  applying the cosmetic composition to human hair; and
  rinsing the cosmetic composition from the human hair or skin;
  wherein the silicone and cosmetic compositions are according to claim 1.

16. A method of increasing the smoothness, silkiness and/or shine of human hair, said method comprising:
  incorporating a silicone composition in a shampoo, conditioning composition, or colouring product to form a cosmetic composition;
  applying the cosmetic composition to human hair; and
  rinsing the cosmetic composition from the human hair or skin;
  wherein the silicone and cosmetic compositions are according to claim 1.

17. The method according to claim 14, further comprising the step(s) of lathering and/or rubbing the cosmetic composition into the human hair or skin by hand, and wherein the step of rinsing is further defined as rinsing the cosmetic composition from the human hair or skin by hand.

18. The method according to claim 15, further comprising the step(s) of lathering and/or rubbing the cosmetic composition into the human hair or skin by hand, and wherein the step of rinsing is further defined as rinsing the cosmetic composition from the human hair or skin by hand.

19. The method according to claim 16, further comprising the step(s) of lathering and/or rubbing the cosmetic composition into the human hair or skin by hand, and wherein the step of rinsing is further defined as rinsing the cosmetic composition from the human hair or skin by hand.

20. A method of producing a cosmetic composition for application to a keratinous substrate of a human, said method comprising:
  (i) dispersing a finely divided solid hydrophobic filler in a hydrophobic organopolysiloxane fluid having a surface tension of from 15 to 40 mN/m to prepare a silicone composition; and
  (ii) mixing the silicone composition with a cosmetically active ingredient in a cosmetically acceptable medium to produce the cosmetic composition;
  wherein the cosmetic composition is a foamable composition such that a foam or lather forms during application to and/or use on a keratinous substrate.

* * * * *